United States Patent [19]

Deinlein-Kalb

[11] 4,194,390
[45] Mar. 25, 1980

[54] METHOD OF AND APPARATUS FOR ASCERTAINING THE STATE OF AGGREGATION OF A MEDIUM

[75] Inventor: Hans Deinlein-Kalb, Nüremberg, Fed. Rep. of Germany

[73] Assignee: Klinger AG, Zug, Switzerland

[21] Appl. No.: 905,180

[22] Filed: May 10, 1978

[30] Foreign Application Priority Data

May 11, 1977 [AT] Austria .................................. 3382/77

[51] Int. Cl.² ............................................. G01N 15/06
[52] U.S. Cl. ...................................... 73/61 R; 137/842
[58] Field of Search ........................... 73/61 R, 19, 53; 137/842, 183, 393

[56] References Cited

U.S. PATENT DOCUMENTS

| | | | |
|---|---|---|---|
| 3,269,404 | 8/1966 | Lebow | 137/393 |
| 3,678,733 | 7/1972 | Blatter | 73/54 |
| 4,004,604 | 1/1977 | Deinlein-Kalb | 137/183 |

*Primary Examiner*—Anthony V. Ciarlante
*Attorney, Agent, or Firm*—Haseltine, Waters & Lake

[57] ABSTRACT

A method of ascertaining the state of aggregation of a medium, whereby the flow of the medium is directed to a first of a series of two or more coaxially arranged nozzle means, further the initial pressure of said medium ahead of said series of nozzle means is compared with a further pressure, said pressure generated when following nozzles are flowed at directly through a respective preceding nozzle via a closed space arranged between two or more nozzles or following the final nozzle, and the correspondingly generated differential pressure is utilized as measurement value for indication of the state of aggregation and if necessary directly or indirectly for controlling the flow of said medium. The apparatus for carrying out the method comprises a casing means having an inlet port means and an outlet port means for a flowing medium, comprises further an inlet chamber means, an intermediate chamber means and a final chamber means arranged in succession, whereby said chamber means are separated from each other by wall means and every one of said wall means comprises a nozzle bore means arranged coaxially relative to each other, whereby further said inlet chamber means is in communication with said inlet port means and at least a part of the intermediate chamber means or the final chamber means is in communication with said outlet port means, and whereby the mutual distance between two adjacent nozzle bore means is not larger than a value ten times larger than the diameter of the inlet diameter of the nozzle bore flowed at.

7 Claims, 14 Drawing Figures

METHOD OF AND APPARATUS FOR ASCERTAINING THE STATE OF AGGREGATION OF A MEDIUM

BACKGROUND OF THE INVENTION

1. Field of the Invention

The present invention relates to a method of ascertaining the state of aggregation of a medium and to an apparatus for carrying out said method.

2. Description of the Prior Art

A conventional method and apparatus for carrying out said method has been applied for condensate draining and has been operating in accordance with the so-called cascade principle. In such apparatus a certain intermediate pressure depending on the particular medium used is built up in a chamber or space between two orifices, said intermediate pressure attaining a value between the inlet pressure ahead of the first orifice and the discharge pressure after the second orifice, whereby this intermediate pressure is then utilized in the control of the condensate discharge apparatus. Thereby both such orifices are arranged at a considerable distance from one another and hardly coaxial to one another such that the divergence of the jet pattern of the medium leaving the first nozzle, which divergence depends largely on the state of aggregation of the medium, does in no way influence the mentioned intermediate pressure. Such cascade condensate discharge apparatus features the drawback, that the utilizable differential pressures specifically at high temperatures (e.g. in case of a comparison between boiling water and saturated steam) are quite small and that changes of diameters of a bore defining an orifice due to deposits or erosions alter to such an extent that an exact ascertaining of the state of aggregation of a particular medium is no longer possible.

SUMMARY OF THE INVENTION

An object of the invention is to provide a new method of ascertaining the state of aggregation of a medium in that the flow of the medium is directed to a first of a series of two or more coaxially arranged nozzle means, further in that the initial pressure of said medium ahead of said series of nozzle means is compared with a further pressure, said pressure appearing when the following nozzles are flowed at directly through a respective preceding nozzle in a closed space arranged between two or more said nozzle means or following the final nozzle means, and the correspondingly appearing differential pressure is utilized as a measurement value for indication of the state of aggregation and if necessary directly or indirectly for controlling said medium.

Another object of this invention aims at the provision of a new and improved apparatus for ascertaining the state of aggregation of a medium, which apparatus includes the features that there is provided a casing means having an inlet port means and an outlet port means for a flowing medium, further an inlet chamber means, an intermediate chamber means and a final chamber means arranged in succession, whereby said chamber means are separated by wall means and each of said wall means comprises a nozzle bore means arranged coaxially relative to each other, further that said inlet chamber means is in communication with said inlet port means and at least a part of the intermediate chamber means or the final chamber means is in communication with said outlet port means, and in that the mutual distance between two adjacent nozzle bore means is not larger than a value ten times larger than the diameter of the inlet diameter of the nozzle bore flowed at.

The present invention is based upon the concept that the jet of a medium flowing out of or leaving a nozzle features a conically diverging pattern varying according to the state of aggregation or intermediate mixture states of said medium. In case the medium is a liquid, the degree of conical divergence is the smallest; the degree of conical divergence increases in proportion to the amount of gaseous parts admixed with the liquid medium, whereby the largest conical divergence, i.e. largest angle of the apex of the cone-like jet is attained in case pure gas flows through said nozzle. In case such a nozzle is followed by a second nozzle such that the jet exiting the first nozzle flows directly to the second nozzle a more or less large portion of the jet exiting from the first nozzle will flow depending on the state of the medium through the second nozzle and thus influence the state of the pressures in the spaces ahead of and beyond this second nozzle. The present invention is now based on the recognition that the comparison of these states of the pressure with the initial or entry, respectively, pressure of the medium can be directly utilized for ascertaining the state of aggregation.

In the space between two nozzles of a preferred embodiment of the inventive apparatus the dynamic pressure will vary proportionally to the amount of gas contained in the liquid medium; accordingly, if a pure gas flow is present the dynamic pressure ahead of the nozzle flowed at will attain its highest value, whereas the pressure in the space behind a nozzle flowed at will be the larger in comparison with such pressure before said nozzle the higher the amount of gas present in the liquid medium is. It has been specifically found that at an application of the inventive method for saturated steam the differential pressure changes proportionally to the wetness of the steam. Thus the inventive method is suitable for use in the technology of measuring and controlling, such as e.g. as measuring and control value for the state of aggregation, wetness of the steam, condensate discharge, deaeration, liquid level control, etc.

The mutual distance between two adjacent nozzle bores of a preferred embodiment of the apparatus is three to six times the diameter of the flowed at nozzle at the entrance side thereof. If the diameter of at least one flowed at nozzle bore decreases conically from inlet to exit thereof, evaporation of the jet of a heated, liquid medium is substantially decreased.

In contrast with the earlier mentioned cascade discharge apparatus any change of diameter of the nozzles of the inventive apparatus during its operation has no influence on the measurement range of the inventive method and is several times larger than that of the cascade method.

Control members or armatures, respectively, or other device for measuring or utilizing the differential pressure can be directly controlled by the inventive apparatus, if it, on the one hand, is in communication with the inlet chamber and, on the other hand, in communication with the final chamber or intermediate chamber, respectively.

On the other hand it is possible to utilize in accordance with a further embodiment the dynamic pressure behind two nozzle bores of the apparatus itself for controlling, depending on the state of aggregation, whereby a control member having an axially extending through bore comprising two nozzle-like sections of reduced inner diameter is axially moveable arranged in a casing, which control member is, in the general area of one end, sealed against the casing and in the general area of the opposite or other end forms a closure part for a valve seat provided inside said casing, whereby the diameter of the valve seat is smaller than the diameter of the one end section sealed against the casing. In such casing there is provided an inlet port for the medium which is in communication with the one side of the valve seat, and furthermore there is provided an outlet port for the medium which is in communication with the other side of the valve seat as well as with the section of the through bore through the control member arranged between the two nozzle-like sections of reduced diameter.

In a preferred embodiment useable for discharging liquids out of a space filled with gas or the like it is preferred to arrange the closure part at a section of reduced diameter of the control member, which section extends through the valve seat. In case of a further preferred embodiment for discharging gas from a space containing a liquid there is preferably arranged a section of reduced diameter at the opposite end of the control member forming directly the closure part of the valve seat.

According to a further embodiment the pressure prevailing between said two nozzles is utilized for control, whereby a control member provided with an axially extending through bore is axially moveable arranged in a casing. The through bore comprises one nozzle-like section of reduced inner diameter and is at one end section sealed against the casing and forms at the other end section a closure part for a valve seat arranged inside the casing. The diameter of the valve seat is smaller than the diameter of the first at the sealing location. One of the two openings in the casing defining the inlet and outlet, respectively, ports is in communication with one side of the valve seat and the other opening is in communication with the other side of the valve seat and one an bore. This nozzle bore is arranged in the casing coaxially in an extension of the nozzle-like section of reduced inner diameter of the through bore of the control member.

Because in this embodiment the pressure prevailing between the two nozzles is utilizable for controlling the control member it is basically feasible to use any of the two openings in the casing as inlet or outlet, respectively. The arrangement chosen depends obviously from the specific object and accordingly, the diameter of the valve seat and the diameter of the sealing section of the control member are to be determined.

BRIEF DESCRIPTION OF THE DRAWINGS

The present invention will be more fully understood by reference to the following detailed description thereof, when read in conjunction with the attached drawings, and wherein.

DETAILED DESCRIPTION OF THE PREFERRED EMBODIMENT

Figure 1:
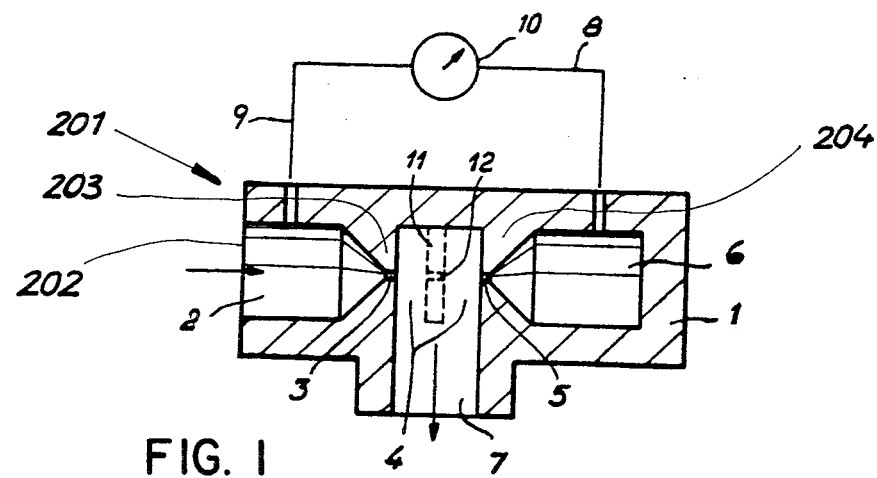
FIG. 1 is a schematic cross-section through a preferred embodiment used for a direct controlling of measuring and control devices.

Referring now to the drawings, and considering initially the exemplary embodiment of measuring apparatus 201 as shown in FIG. 1, it will be understood that the same comprises a housing 1 provided with an inlet port 202 which constitutes at the same time the inlet chamber 2 of the apparatus, an intermediate chamber 4 and a final chamber 6, whereby the intermediate chamber 4 is open towards the exit port 7. In this embodiment the individual chambers 2, 4 and 6 are separated from each other by rigid walls 203 and 204, whereby in wall 203 there is provided a nozzle hole 3 and in wall 204 there is provided a nozzle hole 5, the nozzle holes 3 and 5 extending coaxially to each other. The inlet chamber 2 is connected by means of a conduit 9 to a pressure differential gauge member 10 and the final chamber 6 is connected by means of a conduit 8 with said pressure differential gauge member 10. If now a liquid medium flows into the inlet chamber 2 such liquid will flow through the first nozzle 3, from which it will flow through the intermediate chamber 4 forming therein an only slightly diverging jet pattern and from chamber 4 it will flow into the second nozzle 5. Consequently, a dynamic pressure corresponding closely to the pressure prevailing in the inlet chamber 2 will be generated within the final chamber 6. In case a liquid medium mixed with a gaseous medium is led into the inlet chamber 2 there will be formed in the intermediate chamber 4 a comparably widened jet pattern such that only a portion of this jet reaches the second nozzle 5, whereby a comparably lower dynamic pressure will be generated in the final chamber 6. If gas or superheated steam, respectively, is admitted into inlet chamber 2 a dynamic pressure will be generated in the final chamber 6 which is merely a fraction of the pressure prevailing in the inlet chamber 2. Accordingly, the pressure differential gauge 10 indicates in addition to the differential pressure simultaneously the state of aggregation or state of mixture, respectively, of the medium or mixture, respectively. In this embodiment a further wall 11 shown by broken lines extends into the intermediate chamber 4, in which further wall 11 a further coaxially extending nozzle hole 12 is provided, such that in case of a flow of a gaseous medium a further resistance to the flow comes into force.

Figure 2:
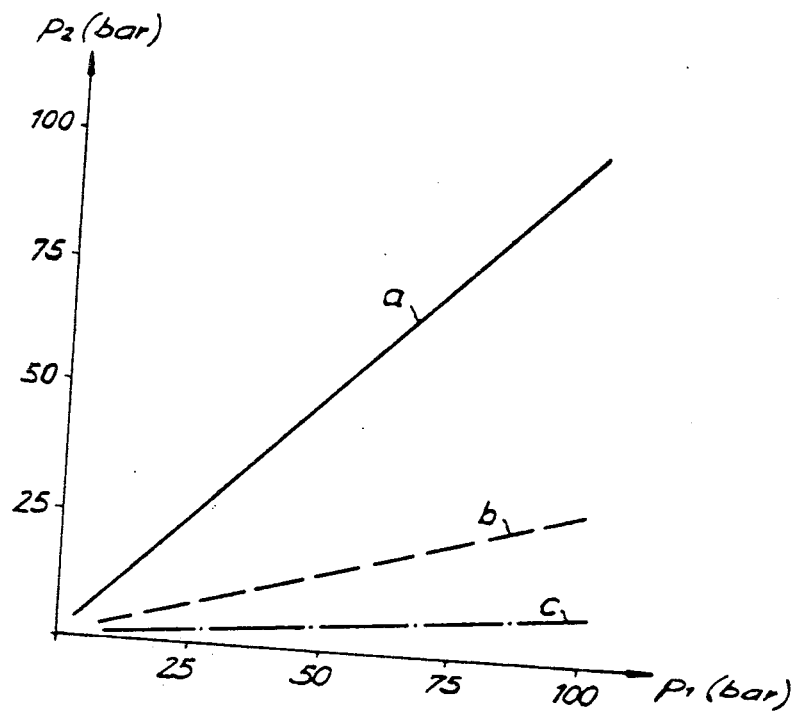
FIG. 2 is a graph showing characteristic pressure curves.

FIG. 2 shows a typical pressure distribution diagram of an embodiment of measuring apparatus 201 according to FIG. 1. Thereby $p_1$ denotes the pressure prevailing in the inlet chamber 2 and $p_2$ denotes the pressure prevailing in the final chamber 6; curve (a) corresponds to the pressure distribution in case of cold water, curve (b) corresponds to same in the case of boiling water and finally, curve (c) corresponds to same in case of a pure gas or superheated steam, respectively. This diagram discloses firstly that, at the same pressure prevailing in the inlet chamber $p_1$, the pressure $p_2$ generated in the final chamber 6 is substantially higher for liquid media in comparison with gaseous media; furthermore it is obvious that by means of the inventive apparatus not only the state of aggregation is displaced by means of the differential pressure but also differences in temperature and wetness or moisture (by fluctuations between lines a and b or b and c, respectively).

In case now of the embodiment of the apparatus shown in FIG. 3, denoted generally by the numeral 204, the exit port 7 is in communication with the final chamber 6 and, furthermore, the pressure differential measuring gauge 10 is in communication on the one hand by means of conduit 9 with the inlet chamber 2 and on the other hand by means of conduit 8 with the intermediate chamber 4, a situation is produced which is contrary to the situation prevailing in the apparatus 201 of FIG. 1. Accordingly, the highest differential pressure will be generated in the case of liquid media flowing through apparatus 204 and the lowest differential pressure is generated in the case of gaseous media.

Figure 3A:
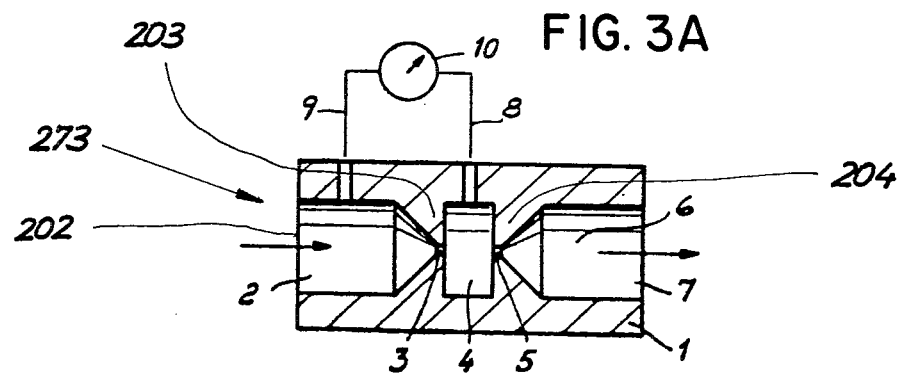
FIG. 3A is a schematic cross-section through a further preferred embodiment used for a direct controlling of measuring and control devices.
Figure 3B:
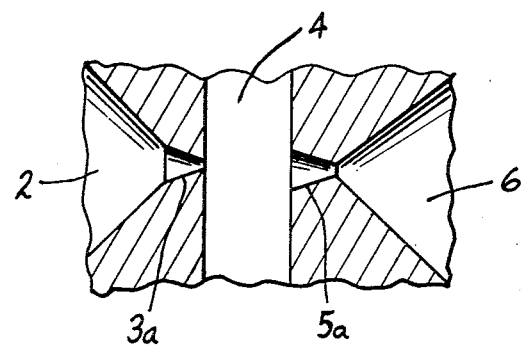
FIG. 3B is an enlarged partial schematic cross-section through a preferred embodiment of the nozzles in FIG. 3A.

It is, furthermore to be noted that in the foregoing embodiments, such as is the case in the following embodiments, the nozzle openings are designed in most of the figures as being of a cylindrical configuration and of the same cross-sectional area as shown by nozzles 3 and 5 in FIGS. 1 and 3A. This design is however not mandatory and depends rather on the specific operational conditions with regard to the media used and to the pressures and the temperatures thereof. In case of media having a high temperature it is specifically advantageous to design the nozzles such that their cross-sectional area has a conical convergence in the direction of flow as shown by nozzles 3a and 5a in FIG. 3B, because in such case evaporation of the medium is curtailed. However, in all embodiments it must be ascertained that all nozzles will indeed be flowed against directly by the exiting jet of at least the liquid medium; this will not be the case in practically all such cases when the distance between two adjacent nozzle holes exceeds a value above 10 times the diameter of the inlet diameter of each nozzle opening flowed against (whereby obviously the nozzle itself can vary conically in direction of the flow).

Figure 4:
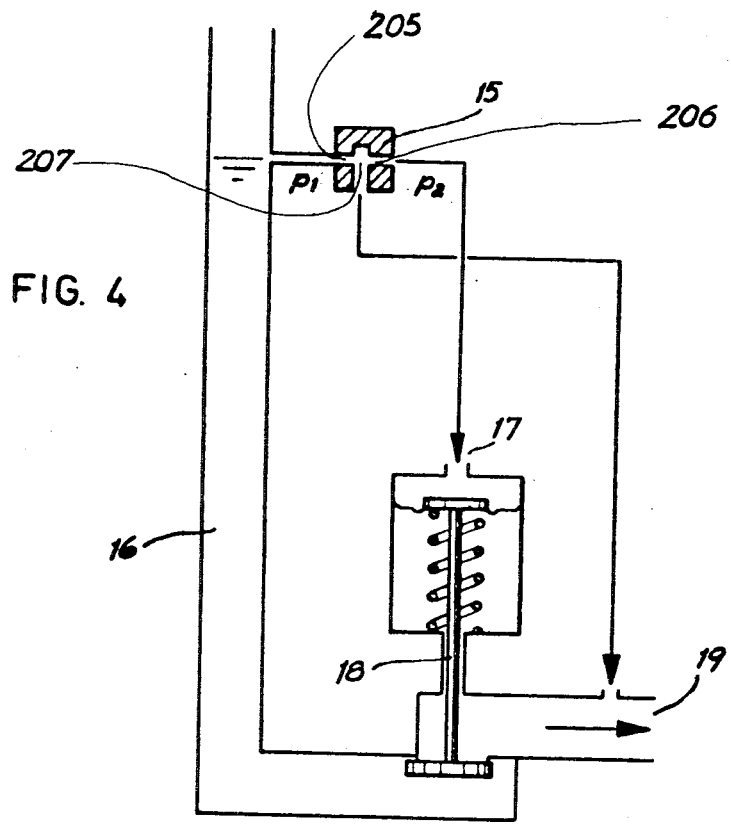
FIGS. 4 and 5 are schematic control circuits of preferred applications of preferred embodiments.
Figure 5:
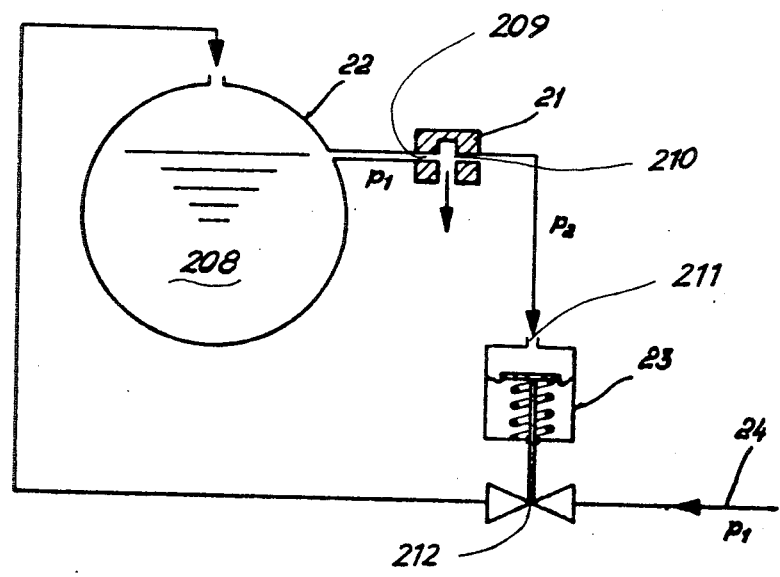

In FIG. 4 and embodiment of the apparatus of FIG. 1 is shown schematically and used in an application of an automatic discharge of large quantities of condensate. Thereby the inlet chamber 205 of this apparatus 15 is in communication with conduit 16 in which a condensate flows, and the final chamber 206 is in communication with the regulating port 17 of a diaphragm valve 18. Thus, the dynamic pressure $p_2$ which is generated in the final chamber 206 acts directly on the drive of the valve 17, which valve 17 remains open as long as the apparatus 15 is flowed at by a liquid condensate; thereby the intermediate chamber 207 is in communication with a low pressure drain line 19 in accordance with FIG. 1. In FIG. 5 an embodiment 21 of the inventive apparatus is shown operating as a device for controlling the level of a liquid arranged in a container 22. The inlet chamber 209 of the apparatus 21 is arranged at the desired level of the interior of the container 22, and the exit chamber 210 is in communication with the regulating port 211 of a diaphragm valve 23, which valve 23 will open only if the pressure prevailing in the exit chamber 210 decreases in case a gas flows through the apparatus which opens the shutoff valve 212 of an infeed conduit 24 leading to the container 22. As soon as the liquid level inside the container 22 is high enough to cause liquid to flow into the apparatus 21 the valve 212 will shut off the infeed conduit 24.

Although the embodiment 201 disclosed in FIG. 1 has been described with reference to the applications shown in FIGS. 4 and 5, it is as well possible to operate the embodiment 201 in accordance with the apparatus 104 of FIG. 3. It is to be specifically noted that the flow of the medium through the apparatus of the invention is an uninterrupted or continuous flow. However, the losses suffered thereby by the flowing medium are practically neglectably small, provided that the nozzle holes are correctly dimensioned and selected correspondingly small.

Figure 6:
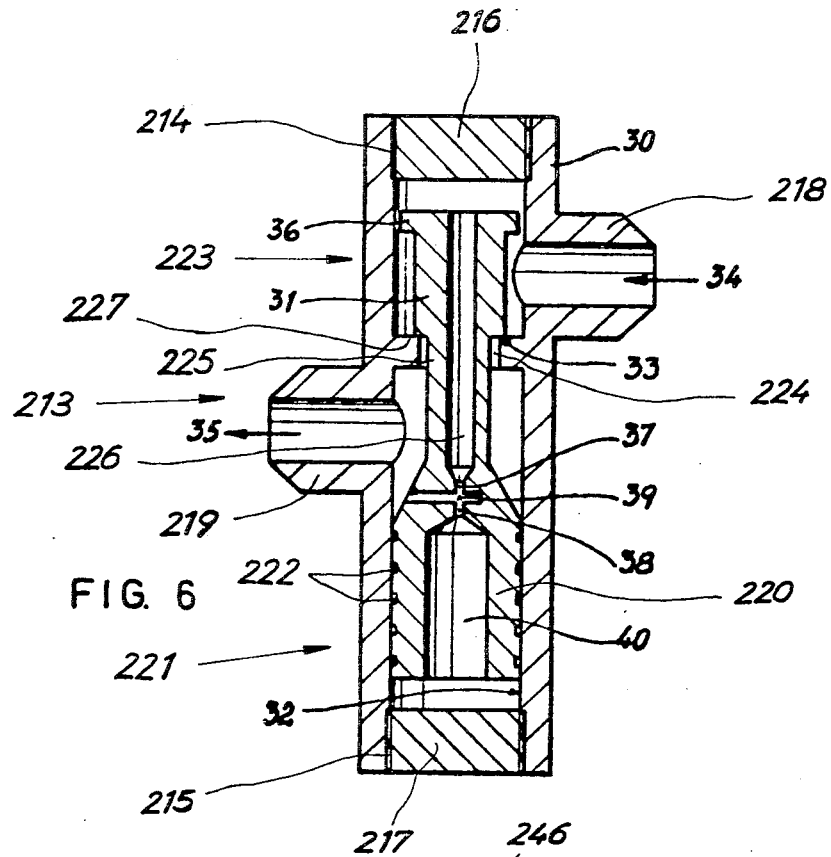
FIGS. 6–13 are sections through preferred embodiments, whereby the control of the medium depending on the state of aggregation is carried out in the apparatus itself.

In FIG. 6 there is shown an embodiment of the inventive apparatus designed as a condensate draining device 213 which controls directly the flow of the medium. This condensate draining device 213 comprises a cylindrical casing 30 provided at both ends with inner threads 214 and 215, respectively, in which end plugs 216 and 217, respectively, are threadingly and sealingly received. The cylindrical casing 30 is provided with a first short pipe stub 218 defining an inlet port 34 and with an oppositely located second short pipe stub 219 defining an outlet port 35. In the bore 32 of the casing 30 an axially moveable control member 31 is arranged and having a first lower end section 220 arranged with a sliding fit in bore 32 at the lower end section 221 of the casing 30, whereby this end section 221 is sealed by labyrinth seals 222 against the bore 32.

At the opposed, upper end section 223 of the casing 30 a valve seal 33 is arranged. The upper section 225 of the control member 31 penetrates the bore 224 of the valve seat 33, which valve seat 33 is at one side in communication with the inlet port 34 and on the other side in communication with the outlet port 35. An enlarged section 36 at the uppermost end of the control member 31 operates as a streamline filter for the medium entering the apparatus 213. The control member 31 is provided with an axially extending through bore 226. This through bore 226 comprises two nozzle-like reduced sections 37, 38, whereby the space 39 therebetween forms the intermediate chamber and is in communication with the exit port 35. The pressure rise proceeds in accordance with that described above with reference to FIG. 1, whereby in the embodiment 213 of FIG. 6 the pressure generated in the final chamber 40 in the end section 220 causes the control member 31 to move axially of the casing 30 in turn causing an opening or closing of the valve seat 33. Therefore, as long as a medium flows through this condensate draining device 213 there exists also in the final chamber 40 a high pressure corresponding closely to the pressure prevailing at the inlet 34, such that the sealing area 227 of the control member 31 clears the valve seat 33, this because the cross-sectional area of the sliding fit at the lower end section 220 of the control member 31 exceeds the cross-sectional area of the valve seat 33 resulting in a generation of a sufficiently large opening force.

As soon as a gas or steam flows through both nozzle holes 37 and 38 the pressure prevailing in the final chamber 40 decreases such that the control member 31 under the influence of the inlet pressure acting thereupon will be shifted towards the valve seat 33 and thus shuts off the flow of the medium.

Figure 7:
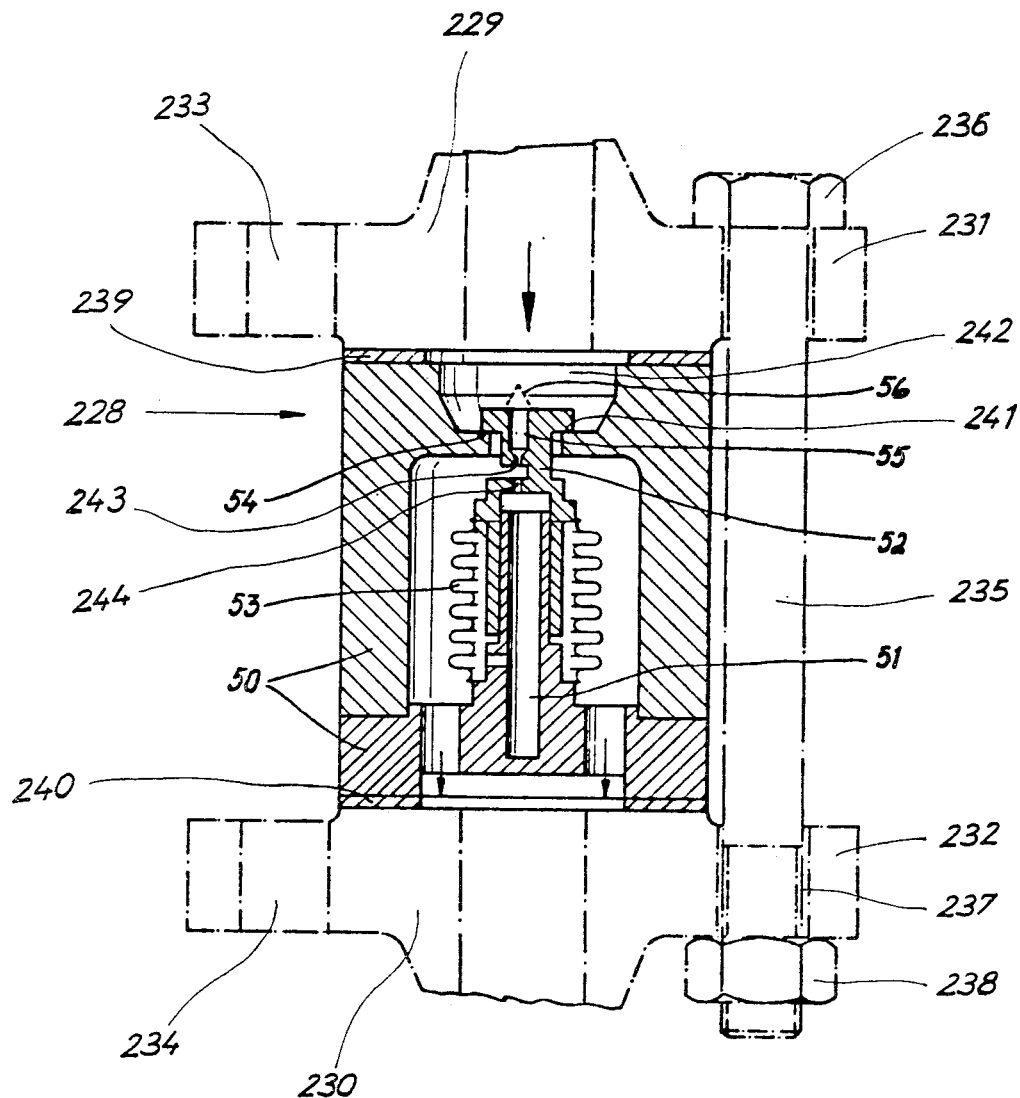

In FIG. 7 a further embodiment of the inventive apparatus is shown, designated generally with the reference numeral 228. This apparatus 228 operates analogously to the apparatus 213 shown in FIG. 6 and described above. The apparatus 228 of FIG. 7 is mounted between two gas or steam pipes 229 and 230, respectively. In FIG. 7 the end flanges 231 and 232, respectively, of the pipes 229 and 230, respectively, are shown, whereby said end flanges 231 and 232 are in a known way each provided with a plurality of through bores 233, 234. A plurality of tension rods 235 provided at one end with a hexagonal head 236 and at the other end with a thread 237 are inserted in pairs of corresponding bores 233 and 234 and each provided at said opposite ends with a hexagonal nut 238, such that upon tightening the nuts 238 the apparatus 228 is fixedly secured between the two flanges 231 and 232. Between the casing 50 of the apparatus 228 and the flange 231 there is provided a sealing ring 239 and a corresponding sealing ring 240 is arranged between the casing 50 and the other flange 232.

The main difference between the apparatus 228 of FIG. 7 and the apparatus 213 of FIG. 6 is the fact that former apparatus 228 comprises a gastight metal bellows 53 forming the seal against the casing 50 such as to define the final chamber 51 between casing 50 and control member 52. Accordingly, the leakage rate of the closed position of the valve is comparably smaller than that of the embodiment shown in FIG. 6, whereby the end section 54 of the control member 52, cooperating with the valve seat 241 does not form a streamline filter; instead of such filter a cone-shaped screen 50 is inserted at the inlet port 242 into a bore 55 extending through the control member 52 thus filtering contaminants out. Due to this design the cross-sectional areas of the individual nozzles 243 and 244 can be kept quite small such that the volume of steam necessary for controlling or operating, respectively, the valve is extremely small. During the open state of this discharge apparatus 228 the liquid flowing therethrough acts continuously upon the screen 56 and thus the screen 56 is continuously cleaned.

Figure 8:
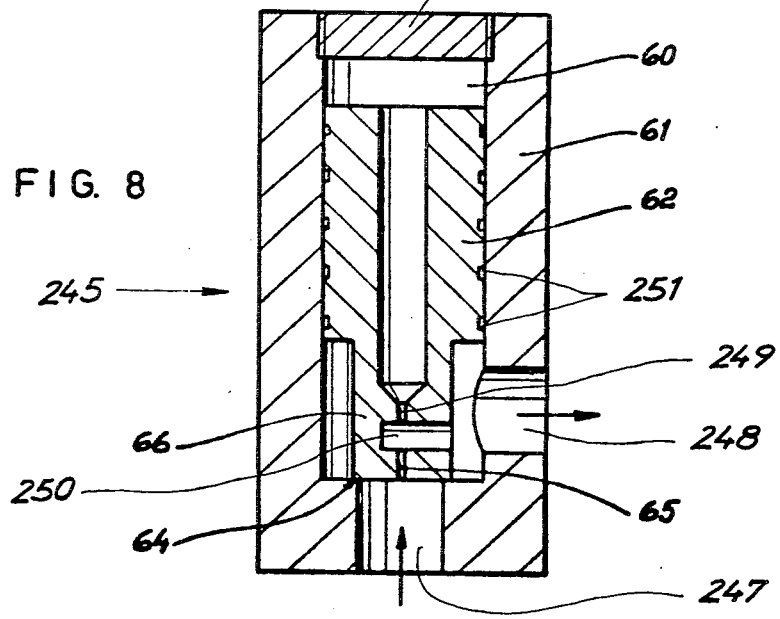

In FIG. 8 there is shown an apparatus 245 which is analogous to the apparatus 213 of FIG. 6. The apparatus 245 comprises again a casing 61, a final chamber 60 and a control member 62. The casing 61 is a cylindrical part closed at one end by a threaded plug 246. The casing is provided with an axially extending inlet opening 247 and a laterally extending outlet opening 248. Again, there is provided a first nozzle 65 and a second nozzle 249 and an intermediate chamber 250. The control member 62 seals by means of a series of labyrinth seals 251 against housing 61 such that the pressure prevailing in the final chamber 60 is utilized for an automatic control of the apparatus 245. In this embodiment 245, however, the reduced end section 66 of the control member 62 does not project through the valve seat 64; it rather acts directly thereupon such that if a liquid flows through this apparatus 245 it remains substantially closed, however it moves into an open position as soon as there is a gaseous flow, because in such case due to the large divergence of the jet pattern after the first nozzle 65 practically no pressure rise in the final chamber 60 will occur. Accordingly, this apparatus operates as an automatic venting valve.

Figure 9:
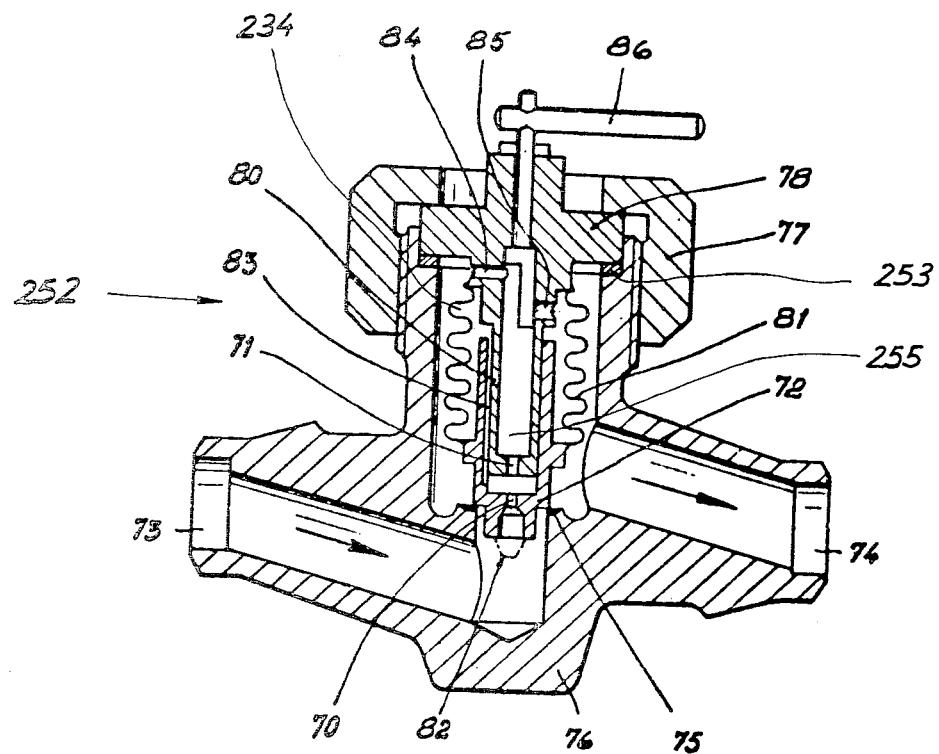

In FIG. 9 there is shown a further embodiment of the inventive apparatus identified by the reference numeral 252. In this apparatus 252 the pressure prevailing between the two nozzles 70, 71, said pressure depending on the state of aggregation of the medium, is utilized to control or operate, respectively, the control member 72. The housing 76 comprises an inlet 73 and an outlet 74, and therebetween there is arranged a valve seat 75. The control member 72 extends coaxially to the valve seat 75 and is arranged axially moveable inside the casing 76. This control member 72 is guided in a closure cap 78 mounted by means of a screw cap 77 to the casing 76. A sealing ring 253 is arranged between the closure cap 78 and the casing 76. This control member 72 is slidably guided along a hollow spindle 80 forming a part of the closure cap 78 and comprising at one end the second nozzle hole 71. The control member 72 is mounted to a bellows 81 mounted in turn to the closure cap 78 of the casing 76, thus the control member 72 is gastight, however slidably mounted to the closure cap 78, whereby the operational cross-sectional sealing area exceeds the area of the valve seat 75. The control member 72 is provided at its end portion cooperating with the valve seat 75 with an axially extending bore hole defining a first nozzle hole 70 and is, furthermore, protected by a screen filter 82. The pressure generated between the two nozzles 70, 71 acts due to the provision of a groove 83 between spindle 80 and control member 72 also in the space 234 within the bellows 81. The space 255 inside the spindle 80 of the closure cap 78 communicates on the one hand with the exit port 74 by means of a bore 84 and on the other hand with the space 254 within the bellows 81 by means of a bore 85, whereby the two bores 84, 85 can selectively be shut off by means of a rotatable control device 86. In the position of the control device 86 shown in FIG. 9 the inner space 255 of the spindle 80 is in communication with the exit port 74, such that there is generated a pressure rise analogous to that in the apparatus 204 of FIG. 3. If steam flows through the nozzles 70, 71 a high pressure rise is generated between said two nozzles 70, 71 and consequently also at the space 254 inside of the bellows 81, so that the control member 72 is urged against the valve seat 75 and kept in this position. As soon as a liquid flows through the two nozzles 70, 71 the pressure prevailing between these two nozzles 70, 71 decreases substantially, so that the control member 72 rises off of the valve seat 75 and thus completely clears the discharge or drain, respectively. In case the control element 86 is rotated through 90° out of the position shown in FIG. 9 both bores 84 and 85 are open so that the same pressure exists inside as well as outside of the bellows 81 so that the control member 72 opens independently of the state of aggregation of the medium flowing therethrough. In this position a so-called sparging or blowing out of a discharge line is possible. Upon a further 90° rotation of the control element 86 (i.e. a rotation of 180° relative to the position shown in FIG. 9) the communication between the inner space 254 of the bellows 80 and the exit port 74 is cut or shut off, respectively, so that, independent of the state of aggregation of the inflowing medium, a pressure rise is generated in the space 254 inside the bellows 81 so that the apparatus 252 remains closed independently from the state of aggregation of the medium.

Figure 10:
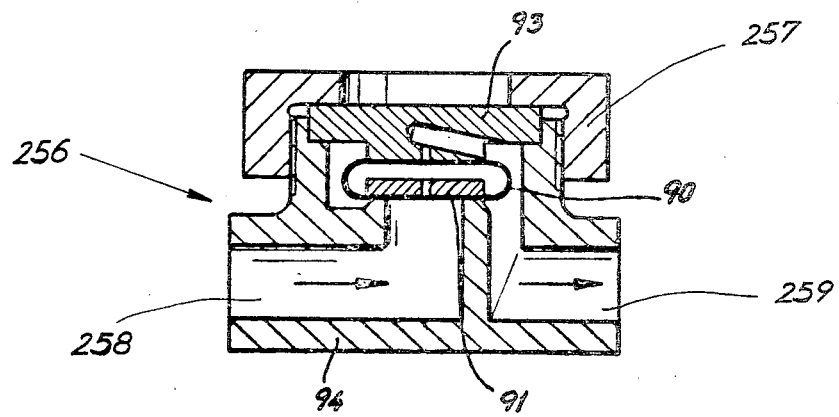

The apparatus 256 shown in FIG. 10 is designed basically similar to the apparatus 252 of FIG. 9, whereby however there exists no possibility of selectively opening or shutting off the apparatus 256 by means of a control element. The bellows 90 comprises only one single undulation, whereby the control member 91 is not mounted in the closure cap 93 of the housing 94, so that a specifically compact design is achieved. This closure cap 93 is held against the casing 94 by a screw cap 257 threadingly engaging the casing 94, which casing 94 comprises as previously an inlet port 258 and an outlet port 259.

The apparatus 260 shown in FIG. 11 operates again similarly to the apparatus 252 shown in FIG. 9 and apparatus 256 of FIG. 10, whereby the sealing between control member 95 and casing 261 is achieved by means of a sliding fit with labyrinth seals 262 at the spindle 96 of the closure cap 97, mounted by screw cap 263 to casing 261. In this closure cap there is provided a threaded bore 264 in which a screw bolt 98 is arranged. By loosening and removing the screw bolt 98 it is possible to have the space 265 beyond nozzle 99 communicating with the outer atmosphere. Thus the medium can be utilized to clear and clean both nozzles 99 and 134 and can be discharged through the top bore 264.

The inlet port of the apparatus 260 is shown by 266 and the outlet port by 267.

The apparatus 260 can however operate also at reverse flow of the medium. Thereby the pressure acting in the direction of opening the valve in case a liquid flows through both nozzles 99 and 268 acts onto the control member 95 in the area between the valve seat 269 and the diameter of the spindle 96. In case the cross-sectional area of the valve seat 269 is half as large as the cross-sectional area of spindle 96 the opening force acting will be the same in both directions of flow of the medium.

Figure 11:
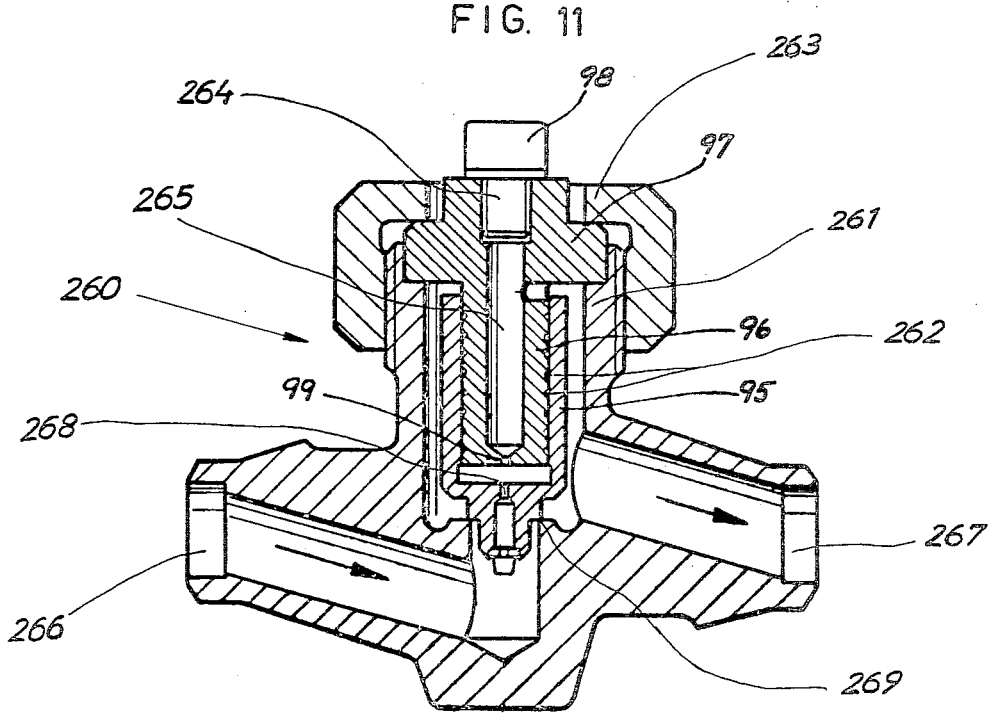
Figure 12:
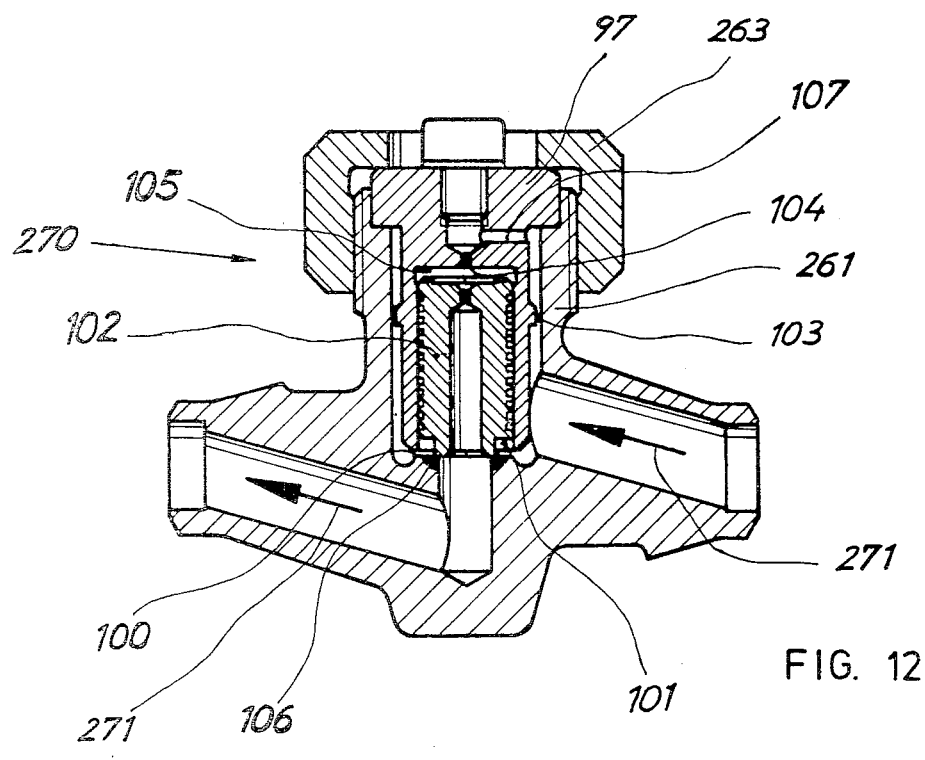

In FIG. 12 a further embodiment 270 of the apparatus operating as condensate draining device is shown, whereby the flow of the medium is reversed in comparison with the aforementioned apparatus of FIG. 11. The pressurized medium flows in the direction shown by the arrows 271. The apparatus comprises a casing 261, a closure cap 97, a screw cap 263 and a threaded bolt 98 similar to the foregoing apparatus 260 and thus a special description thereof is omitted. The pressurized medium acts via a throttling slit 100 acting at the same time as a streamline filter onto the axial annular surface 101 of the control member 102. Filtered pressurized medium is guided via a radially extending throttling slit 103 acting also as a streamline filter and via a lateral bore 107 to the first jet nozzle 104. Accordingly a pressure corresponding to the state of aggregation of the pressurized medium is generated within the cylindrical space 105 and utilized for controlling or operating, respectively, the control member 102.

If the pressurized medium is a liquid, the pressure force acting on the annular surface 101 of the control member 102 predominates and the control member 102 lifts itself off the valve seat 106 and passes the medium towards the discharge.

If the pressurized medium is a gas or is gas-like, then the pressure force prevailing in the cylindrical space 105 predominates and keeps the control member 102 in the closed or shutoff position. During the stroke movements of the control member 102 the axially extending streamline filter 100 functions also as a force degenerative feedback in that at a rising opening stroke of the control member 102 the acting opening force decreases and vice versa due to the throttling action of the throttling slit 100. In this manner a feedback is achieved which secures a smooth and impact-free control of the stroke of the control member.

Figure 13:
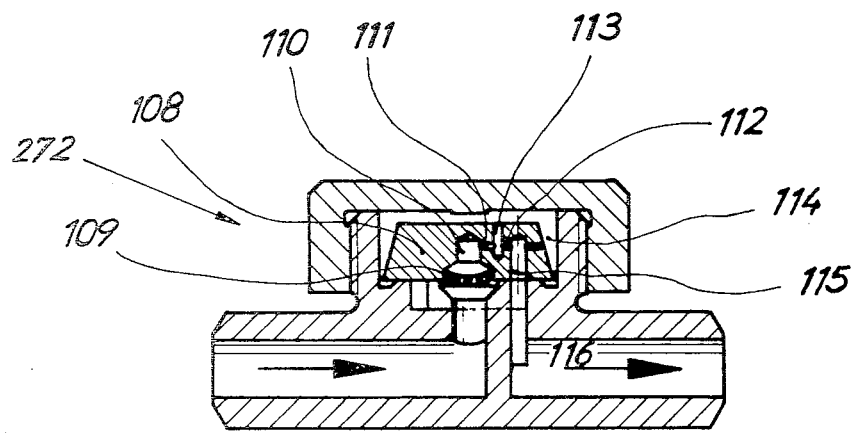

In FIG. 13 there is shown an apparatus 272 which is of a design similar to known thermodynamic condensate discharge devices, whereby however in accordance with the invention the state of aggregate of the pressurized medium contained inside of the cylinder 114 serves exclusively as measuring value. The control member is a control plate 108 with integrated jet nozzles in accordance with the invention. A pressurized medium flows through a screen filter 109 into the center bore 110 and from there through the nozzles 111 and 112 into discharge 115, 116. The pressure generated thereby in the intermediate bore and thus inside the cylindrical space 114 is then in accordance with the invention utilized to act upon and to control the control disc 108.

While there are shown and described present preferred embodiments of the invention, it is to be distinctly understood that the invention is not limited thereto, but may be otherwise variously embodied and practiced within the scope of the following claims.

Accordingly, what is claimed is:

1. A method of ascertaining the state of aggregation of a medium, said method comprising directing a flow of the medium to a first of a series of at least two coaxially arranged nozzles, arranging the nozzles so that the flow from the first nozzle will proceed unimpaired towards the second nozzle, comparing the initial pressure of said medium upstream of said series of nozzles with a further pressure prevailing in a closed space arranged downstream of the first nozzle, and correlating any correspondingly appearing differential pressure as a measurement value for indication of the state of aggregation of the medium.

2. The method as defined in claim 1 wherein the initial pressure of the medium upstream of the series of nozzles is compared with the pressure between the first and second nozzles.

3. The method as defined in claim 1 wherein the initial pressure of the medium upstream of the series of nozzles is compared with the pressure downstream of the last of the nozzles in said series.

4. An apparatus for ascertaining the state of aggregation of a medium comprising a casing means having an inlet port means and an outlet port means for a flowing medium, an inlet chamber means, an intermediate chamber means and a final chamber means arranged in succession, a plurality of wall means separating respective chamber means, and means for measuring said differential pressure, connected, on the one hand, with said inlet chamber and, on the other hand, with one of said final or intermediate chambers, said wall means having respective nozzle bore means arranged coaxially relative to each other in spaced relation such that flowing medium discharged from one of the nozzle means will proceed unimpaired to the second nozzle, said inlet chamber means being in communication with said inlet port means, the intermediate chamber means or the final chamber means being in communication with said outlet port means, the distance between two adjacent nozzle bore means being less than a value ten times larger than the inlet diameter of the nozzle bore means to which the medium is directed after discharge from the other of the nozzle bore means.

5. The apparatus as defined in claim 4 wherein said intermediate chamber means comprises additional wall means having a coaxially arranged nozzle bore means.

6. The apparatus as defined in claim 4 wherein the mutual distance between two adjacent nozzle bore means is three to six times larger than the diameter of the inlet diameter of the nozzle bore means to which the medium is directed.

7. The apparatus as claimed in claim 4 wherein the bore of at least the nozzle bore means to which the medium is directed decreases conically in the direction of flow of said medium.

* * * * *